United States Patent [19]

Maas

[11] 4,243,045

[45] Jan. 6, 1981

[54] METHOD AND APPARATUS FOR THE SUPPRESSION OF INTERFERENCE SIGNALS IN A USEFUL SIGNAL

[75] Inventor: Michael Maas, Uttenreuth, Fed. Rep. of Germany

[73] Assignee: Siemens Aktiengesellschaft, Berlin & Munich, Fed. Rep. of Germany

[21] Appl. No.: 5,865

[22] Filed: Jan. 23, 1979

[30] Foreign Application Priority Data

Feb. 10, 1978 [DE] Fed. Rep. of Germany ....... 2805681

[51] Int. Cl.³ .............................................. A61B 5/04
[52] U.S. Cl. .............................. 128/696; 128/419 PT; 128/901
[58] Field of Search ............... 128/696, 697, 710, 901, 128/419 PT, 698, 708

[56] References Cited

U.S. PATENT DOCUMENTS

| | | | |
|---|---|---|---|
| 3,534,282 | 10/1970 | Day | 128/696 |
| 3,569,852 | 3/1971 | Berkovits | 128/696 |
| 3,599,628 | 8/1971 | Abbenante et al. | 128/698 |
| 3,611,174 | 10/1971 | Day | 128/902 |
| 3,769,965 | 11/1973 | Raodi et al. | 128/419 PT |
| 4,041,328 | 8/1977 | Maas | 128/697 |
| 4,117,848 | 10/1978 | Naylor | 128/419 PT |

*Primary Examiner*—William E. Kamm

*Attorney, Agent, or Firm*—Hill, Van Santen, Steadman, Chiara & Simpson

[57] ABSTRACT

In an exemplary embodiment, the interference signals can occur as a mixture consisting of narrow interference pulse peaks of high amplitude and interference hum. It is desirable that such interference peaks and interference hum in a useful signal be suppressed without mutual influencing. To this end, an occurring useful signal having possibly superimposed interference signals is supplied to an interference hum filter. The filtered-out interference hum component is opposingly superimposed on the original signal for the purpose of compensation of the interference hum. This applies only for such a length of time as there are no interference pulse peaks recognized by a recognition installation. If such an interference pulse peak is recognized, the filter is disconnected from the input signal and switched over to self-oscillation operation. An artificial oscillation with an amplitude and frequency equal to that of the previously selected interference hum component is then generated without a phase jump and superimposed on the useful signal. The interference pulse peak is simultaneously blanked out. The exemplary embodiment can be particularly utilized in the case of electrocardiogram processing for the purpose of suppression of pacemaker pulses and power supply hum.

17 Claims, 10 Drawing Figures

METHOD AND APPARATUS FOR THE SUPPRESSION OF INTERFERENCE SIGNALS IN A USEFUL SIGNAL

BACKGROUND OF THE INVENTION

The invention relates to a method and an apparatus for the suppression of interference signals in a useful signal, wherein the interference signals can occur as a mixture of narrow interference pulses having a high amplitude and interference hum, and whereby the presence of interference pulse peaks and/or interference hum can be separately recognized by means of interference peak and interference hum recognition installations, and, with said recognition, suppressor installations for suppressing the interference pulse peaks and the interference hum in the useful signal are activated.

Particularly in medical technology, wherein e.g. physiological signals are tapped from a patient, interference voltages, such as base line fluctuations, interference voltage peaks resulting from muscle spasms or muscle tremblings, or resulting from artificially supplied stimulation pulses, and mains (or power supply) frequency interferences are frequently observed in the signal derivation as higher-frequency interference hum. Specifically in the case of derivation of an electrocardiogram, pacemaker pulses of a heart pacemaker can also be superimposed on the EKG-signal, in addition to a power supply hum. This applies, in particular, always to those patients who, in order to support their cardiac activity, wear a heart pacemaker. Pacemaker pulses in the EKG are not in every instance an undesired interference voltage; since they are carriers of the information regarding an effected stimulation of the heart, in special instances, it may be desirable, for the purpose of specific evaluation (or analysis), to reproduce EKG-signals together with heart pacemaker pulses. In the normal case; i.e., in common practical application, such as heart frequency measurement, EKG recording or display, etc., however, the presence of pacemaker pulses has a considerably interfering (or disturbing) effect; through the pacemaker pulses, namely, the information content of the EKG signal is generally altered to such an extent that its evaluation (or analysis), whether it be visually by means of the eye, or automatically by means of a suitable evaluation (or analysis) unit, is rendered difficult or even becomes impossible. In these instances, the peak interference voltage; e.g. the pacemaker pulse, must be suppressed in the useful signal.

In general, such an interference peak suppression presents no difficulties insofar as additional interference components such as e.g. the power supply hum are not to be also simultaneously suppressed. An apparatus which permits a suppression of interference pulse peaks in a useful signal; i.e., specifically also of heart pacemaker pulses in an electrocardiogram, is prior knowledge from the British Pat. No. 1,450,081. The suppression of the interference pulse amplitudes however, occurs therein without the simultaneous suppression of an interference hum component. Correspondingly, e.g. the apparatus of the German-AS 2,558,126 also permits only the suppression of power supply hum in the EKG without the presence and simultaneous suppression of interference peaks, such as pacemaker pulses or the like. An apparatus which renders possible a suppression of interference pulse peaks as well as interference hum in a common circuit arrangement is, indeed, already prior knowledge from the U.S. Pat. No. 3,950,694; however, precisely in the case of such a circuit arrangement, reactions of the blanking out of interference amplitude peaks on the suppression of the power supply hum cannot with certainty be precluded in advance. Thus, the danger exists that, during the period of suppression of an interference peak amplitude, the recognition installation, or also the suppression installation for the interference hum may be affected in an uncontrollable manner due to the interruptions occurring, or also due to the jumps in the signal pattern (or progression, or curve). Conversely, however, a useful signal which has not yet, or only insufficiently, been refined of the interference hum has an unfavorable effect in terms of the recognition of interference pulse peaks and their suppression. In the case of heart pacemaker pulses, there then result e.g. difficulties in the compensation particularly of the pacemaker overshoot, since it is hardly possible to convert an EKG with hum interferences into an e-function curve or to derive from the EKG such an e-function curve which is necessary for the exact compensation of the overshoot. In addition, unusually high hum amplitudes can be falsely evaluated as interference pulse peaks by the interference pulse peak-recognition installation, so that this can lead to unnecessary signal suppressions and possibly even signal suppressions which falsify the test result.

SUMMARY OF THE INVENTION

It is an object of the invention to disclose a method and an apparatus of the type initially cited which method and apparatus permit a suppression of such interference signals which manifest in mixture at the worst narrow interference pulse peaks of high amplitude as well as interference hum, whereby mutual influencings, pursuant to recognition and suppression of the one interference signal component, by the respective other interference signal component will with certainty not occur.

The object is achieved with a method of the type initially cited by virtue of the fact that an occurring useful signal with possibly superimposed interference signals is supplied to an interference hum filter for the purpose of filtering out specifically the interference hum only for such a length of time as the recognition installation for narrow interference pulse peaks of high amplitude does not recognize any such interference pulse peaks, and that also only in this instance is the filtered-out interference hum component in the original input waveform counter-superimposed on the useful signal for the purpose of compensation of the interference hum which is superimposed on the latter; however, in case an interference pulse peak is recognized by the recognition installation, the interference hum filter is disconnected from the input signal and is simultaneously switched over to self-oscillation (or natural, or characteristic oscillation), so that it continues to oscillate with the amplitude and frequency of the previously selected interference hum component without a phase jump, and that this artificially produced (or generated) oscillation, finally, at least during the period of suppression of the interference pulse peak, is superimposed of the useful signal for the purpose of compensation of the interference hum. An apparatus which functions according to this method may be inventively characterized by an interference hum filter with an input for the useful signal, possibly having superimposed interference signals, and with an output which is connected to the measuring signal path for the purpose of counter (or opposing) superposition on the useful signal including interference signals of the interference hum filtered out by the filter, whereby the input of the interference hum filter can be disconnected from the input signal via a disconnect switch, which switch can be activated by a switch output of a recognition installation for an interference pulse peak upon occurrence of such a peak, and whereby the interference hum filter, upon switching over into self-oscillation operation, is operative to provide an amplitude and frequency corresponding to that of the previously selected interference hum component without a phase jump upon disconnection of the input from the input signal pursuant to recognition of an interference pulse peak by the recognition installation.

In accordance with the invention, when only an interference hum is superimposed on a useful signal, the latter interference hum is constantly filtered out by the interference hum filter. The interference hum is eliminated through counter (or opposing) superposition on the unfiltered useful signal. The elimination of the interference hum already takes place at the input signal, so that thus a useful signal purified (or refined) of the interference hum is always offered to the recognition installation for the recognition of interference pulse peaks. Thus, an influence of the interference hum on recognition and suppression of interference pulse peaks is no longer provided. However, if an interference pulse peak occurs, a disconnect signal for the interference hum filter is provided directly with the recognition of this interference pulse peak. Thus, the interference pulse peak cannot reach the interference hum filter, as a consequence of which the latter also cannot be impermissibly affected in the pulse response to the interference pulse peak. Although, however, the interference hum filter is disconnected at the input side from the useful signal having possibly superimposed interference hum, so that actually no interference hum is selected any longer, a compensation of the interference hum nevertheless occurs in the useful signal line. This is achieved because the interference hum filter, now in self-oscillation operation, simulates the previously present interference hum component according to amplitude and frequency. If, therefore, prior to disconnection of the interference hum filter, interference hum was also present in the input signal in addition to the actual useful signal, the filter, subsequent to disconnection, continues to oscillate with this interference hum component without a phase jump. The corresponding interference hum component in the useful signal can thus also continue to be compensated. However, if the useful signal contains no or only little hum interference, the output signal of the interference hum filter is virtually equal to zero due to a lack of a sufficiently filterable interference hum component. Consequently, no interference hum component is superimposed on the original signal on the part of the interference hum filter, so that the useful signal, already free of interference signals, insofar as also no interference pulse peaks are present, can proceed unimpeded for further processing and/or display.

Further advantages and details of the invention are apparent from the following description of an exemplary embodiment on the basis of the drawing in conjunction with the subclaims; and other objects, features and advantages will be apparent from this detailed disclosure and from the appended claims.

BRIEF DESCRIPTION OF THE DRAWINGS

FIG. 3 comprising

DETAILED DESCRIPTION

Figure 1:
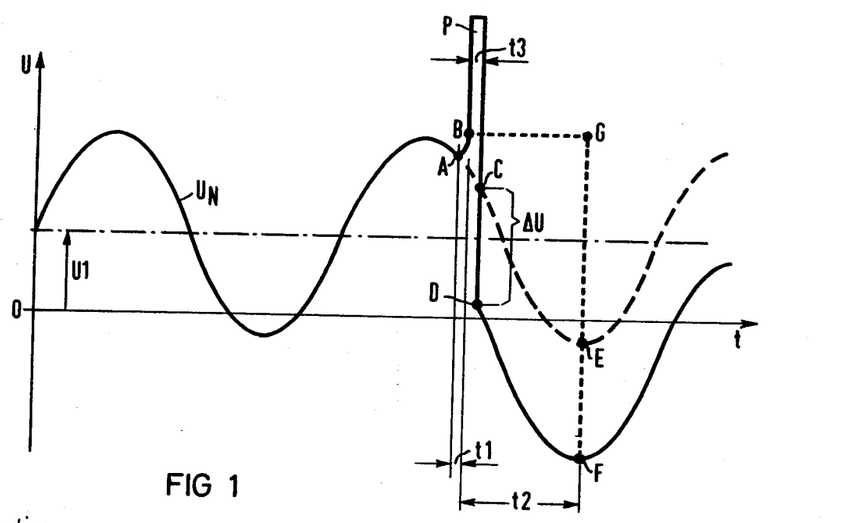
FIG. 1 is an illustration of an EKG-signal as a function of time on which mains frequency interferences and heart pacemaker pulses are superimposed.

FIG. 1 illustrates, in a greatly extended time scale, a fragment of an EKG-signal curve, whereby there is superimposed on the EKG-signal $U_1$ a mains-frequency interference voltage $U_N$ as well as a heart pacemaker pulse P. At point A, the approximately 0.2 to 1 ms ($t_3$)-wide stimulation pulse of the heart pacemaker commences. Its slopes are somewhat obliterated, e.g. conditioned by the properties of the EKG amplifier. Therefore, it is recognized only delayed ($t_1$) at point B. The amplitude of the stimulation pulse is so great that the EKG amplifier is driven to the limit of its output response characteristic. During this time, the EKG contains no additional information; i.e., no statement is possible regarding the actual magnitude of the stimulation pulse, the amplitude of the cardiac action voltage, or the superimposed mains frequency voltage. At best, conjectures can be made here (extrapolation corresponding to the previous history). At the end of the stimulation pulse, the voltage U(t) does not continue its course (or progression) at point C as it would have done without a stimulation pulse. On the contrary, the continuation of the voltage curve (or progression, or course) proceeds at point D which is displaced relative to point C by the voltage $\Delta U$. The voltage difference $\Delta U$ results due to the overshooting of the heart pacemaker pulse; this overshoot decays approximately according to an e-function (time constant, depending upon the type of utilized heart pacemaker, approximately 60 to 250 ms).

From the voltage curve U(t) of FIG. 1 it can be recognized that, during phase $t_2$ of the blanking out of the heart pacemaker pulse, it is impermissible to offer, specifically to the filter for mains frequency suppression, either the solid line represented signal B, C, D, F, or the dotted line represented signal B, G, E, F. In both instances, the filter response would be influenced in an impermissible manner by these voltage curves (or progressions). Thus, in order to avoid this disadvantage, a transient response of the voltage must be offered to the filter which largely corresponds to that particular (or response) which the voltage would have assumed (or taken) if the pacemaker pulse had not occurred. This is the smooth continuation of $U_1$ plus $U_N$ represented by the dash line voltage curve (or progression) A, C, E. In addition, however, also no voltage jump from E to F can be permitted to subsequently take place at the input of the mains frequency filter, because this voltage jump would likewise falsify the filter response. The further voltage progression (or curve) following point E is rather intended to correspond to the input voltage reduced by the amount of the overshooting of the pacemaker pulse.

An additional difficulty consists in that, in order to suppress the pacemaker overshoot, the voltage value at the end of the blanking-out phase must be stored in order that it can subsequently be subtracted from the input signal. To this end, also, the distance E, F, must be known, whereby the point E, however, can be found only by means of extrapolation from point A. The time interval t2 of the blanking-out of a pacemaker pulse is to be of sufficient length, on the one hand, in order that interferences which the stimulation pulse has brought about have died out; however, on the other hand, it is to be as short as possible in order that the extrapolation represented by ash line curve A, C, E, with great probability, corresponds precisely to that particular progression (or curve, or course) which the signal would assume without a superimposed pacemaker pulse. As a compromise, a time span of approximately nine milliseconds (t2=9 ms) is selected.

Figure 2:
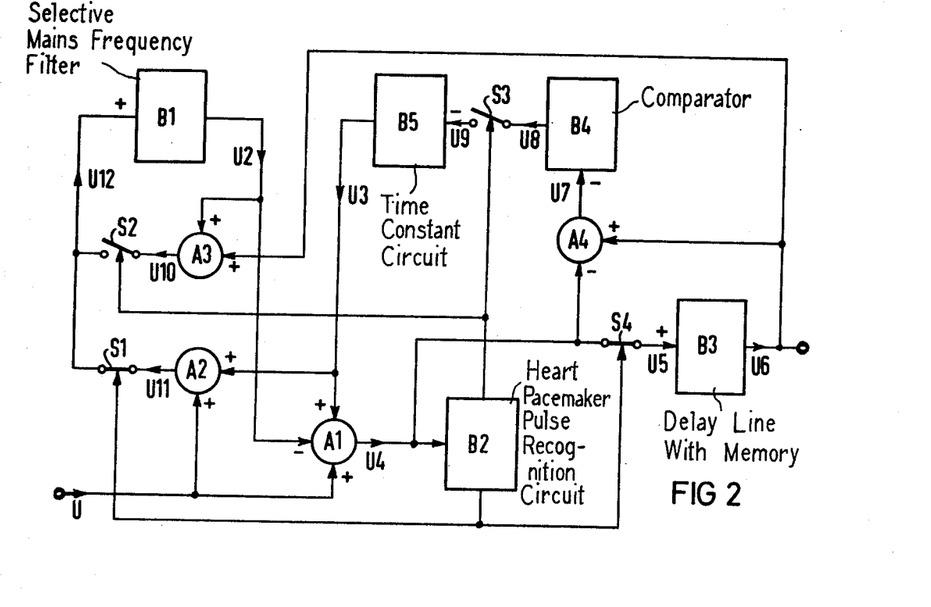
FIG. 2 is a sample embodiment of the invention in a basic circuit diagram.
Figure 3A:
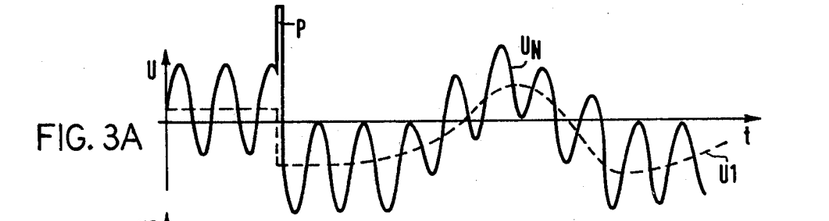
FIGS. 3A-3G illustrates the most essential voltage curves for illustrating operation of the basic curcuit diagram of FIG. 2.
Figure 3B:
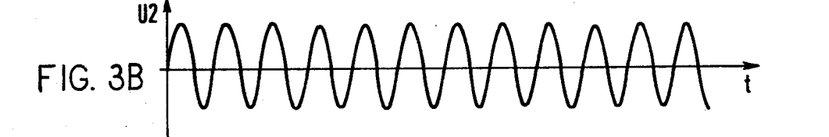
Figure 3C:
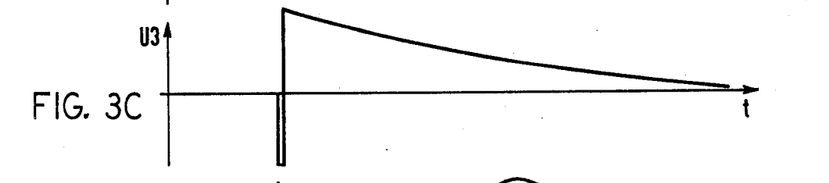
Figure 3D:
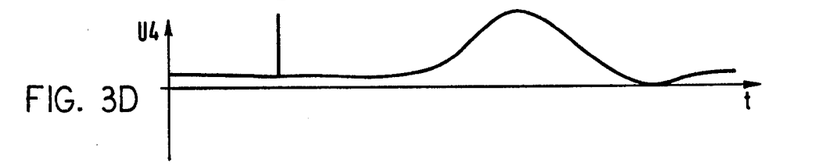
Figure 3E:
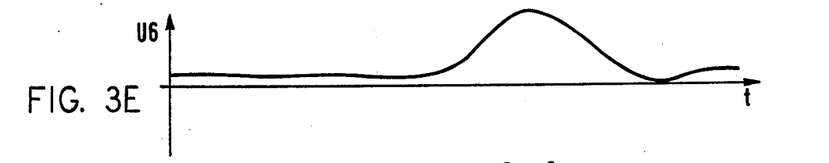
Figure 3F:
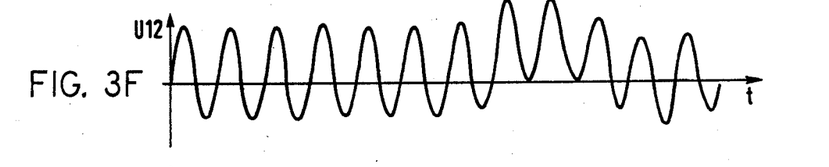
Figure 3G:
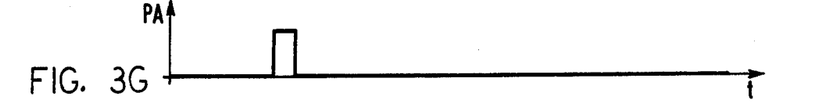

In the basic circuit diagram of FIG. 2, the circuit elements for a selective mains frequency filter are integrated into a subassembly (or structural component) B1, those for the circuit for recognition of a heart pacemaker pulse are integrated into a constructional unit B2, those for a delay line with memory are integrated into a subassembly B3, the circuit elements for a comparator are integrated into a subassembly B4, and finally, the circuit elements for a time constant circuit are integrated into a subassembly B5. Individual subassemblies can be connected with one another by means of analog switches S1, S2, S3 and S4. The subassemblies A1, A2, A3 and A4 are mixing stages for occurring voltage signals.

The basic operational mode of the circuit diagram of FIG. 2 is that within the circuit arrangement of the signal mixture arriving (or occurring) at the signal input EIN is selected for individual signal components of interest. By means of a skillful superimposition of individual voltage components, auxiliary signals are then obtained which largely correspond to the requirement for a true-to-nature simulation of undisturbed signals. The switches S1 through S4 ensure that the auxiliary signals are mixed in the mixing stages A1 through A4 corresponding to the respective instantaneous state of the suppression of a heart pacemaker pulse.

The mode of operation of the basic circuit diagram of FIG. 2 is now to be described on the basis of the essential four instances.

Undisturbed EKG
EKG with mains frequency interference
EKG with pacemaker pulse
EKG with mains frequency interference and pacemaker pulse (a) Undisturbed EKG The undisturbed input signal U=U1 reaches the mixing stages A1 and A2. The voltage U3, which is a characteristic of the presence of a pacemaker pulse, is zero, because a pacemaker pulse is not present. Via the mixing stage A2 and the closed switch S1, the input signal U=U1 reaches, in the form of signal U11=U12, the mains frequency filter B1. Since the EKG-signal is to be undisturbed, the mains frequency portion (or component) $U_N$ in the EKG-signal is also equal to zero or at least very small. Thus, there results, if at all, only an output signal U2 of the selective mains frequency filter B1 which signal is near zero. Thus, virtually only the interference-free EKG-signal component U1 reaches the mixing stage A1, so that the output signal U4 of the mixing stage A1 corresponds to the input signal U1. This signal reaches, via the likewise closed switch S4, the delay line B3 as signal U5. The signal is here delayed and cut off (trimmed) in the frequency range which lies above the range of interest for the undisturbed EKG. The only very slightly changed input signal U=U1 reaches the output AUS of the basic circuit diagram of FIG. 2 as U6. On a (not illustrated) display or recording apparatus; for example, an EKG-recorder or an oscilloscope, the output signal U6 can then be displayed, or recorded, respectively. In addition, or alternatively to this, however, a further processing installation for the EKG signals can also be present at the output AUS. This can be e.g. a heart frequency measuring installation. However, it can also be such an installation which, in addition to or instead of normal QRS-complexes in the EKG, detects and displays such complexes having an extra systolic character.

(b) EKG-Signal With Mains Frequency Interference

The input signal $U=U1+U_N$ reaches, as under case (a), the mixing stages A1 and A2. Since pacemaker pulses are not present, U3 is again zero. U11 at the output of mixing stage A2 corresponds to the disturbed input signal $U=U1+U_N$. This signal reaches, as U12, the mains frequency filter B1 via the switch S1 which is again closed. The mains frequency filter B1 allows only the mains component of the entire signal U12 to pass through. Thus, an output voltage U2 occurs which corresponds according to amplitude and phase to the mains frequency interference in the EKG signal. In the mixing stage A1, this mains signal $U2=U_N$ is subtracted from the input signal $U=U1+U_N$. The output signal U4 of this mixing stage A1 is thus the EKG signal U1 freed of mains frequency interferences. The further progression corresponds to that under case (a) for the undisturbed EKG.

(c) EKG with Pacemaker Pulses of a Heart Pacemaker

As long as no stimulation pulse appears in the EKG signal, the signal is evaluated (or analyzed) according to (a). However, if a pacemaker pulse appears, it is recognized by the pulse recognition installation B2. The recognition installation thereupon produces at its control outputs to the switches S1 through S4 a switch-over pulse which leads to the switching-over (or change-over switching) of the switches S1 through S4 from the illustrated switching state into the other switching state, respectively. The duration of the switch-over pulse here determines the blanking out time duration (t2) for the pacemaker pulse.

Since switch S4 is opened, the output voltage U6 remains at the preceding voltage value. This voltage value, which corresponds to the voltage value in point A according to FIG. 1, is stored in the memory of the constructional unit B3.

The switch S1 opens upon occurrence of a switching pulse of the pulse recognition installation B2. The input signal is thus disconnected from the input of the selective mains frequency filter B1. Thus, in this manner, the pacemaker pulse is kept away (or remote) from the input of the selective mains frequency filter B1. However, switch S2 closes. The stored voltage value is thereby transmitted to the selective mains frequency filter B1 via a feedback line from the output of constructional unit B3, via the mixing stage A3 and the closed switch S2. Thus, in the selective mains frequency filter, the voltage level of the input voltage U directly preceding the pacemaker pulse is simulated.

Switch S3 closes. As a consequence of this, a regulating (or control) loop S3, U9, B5, U3, A1, U4, A4, U7, B4 and U8, also closes. Thus, an output voltage U3 is brought about in the subassembly B5 forming a time constant circuit, which output voltage U3, together with the input voltage U, produces in the mixing stage A1 a voltage which corresponds in amount to the stored voltage value U6, but which is of opposite polarity relative to said voltage value U6. Thus, U3 is exactly the negative value of the input voltage change during the phase of the blanking out of the pacemaker pulse. The time constant-circuit B5 manifests such a time constant that U3 indeed, rapidly adjusts itself to its initial voltage value with the closure of switch S3; however, when, at the end of the blanking-out period, the switch S3 is opened again, the voltage U3 is slowly guided to zero in accordance with an e-function. The slow time constant is adjustable to the time constant of the decay of the overshoot of the heart pacemaker pulse. Thus, with closure of the switch S3, the voltage U3 is adjusted to the peak value of the overshoot of the pacemaker pulse but with opposite polarity. Subsequently, with the re-opening of the switch S3, the voltage U3 decays from this opposite peak value, to zero with the time constant of the overshoot. The superimposition of the original signal U on this signal progression U3 in the mixing stages A1 and A2 effects the compensation of the overshoot of the heart pacemaker pulse in the input signal. Since, with the end of the blanking-out pulse of the pacemaker pulse-recognition installation B2, the switch S1 is also again closed, and the switch S2 is now opened, respectively, there is supplied to the mains frequency filter B1 a signal U12 substantially freed of overshoots of the pacemaker pulse. However, in a corresponding manner, a signal U4 refined (or purified) of overshoots is also produced at the output of the mixing stage A1, which signal U4, via the now again closed switch S4, reaches the delay line B3 and from there, the signal output terminal.

(d) EKG with Mains Frequency Interference and Pacemaker Pulses of a Heart Pacemaker This instance is explained on the basis of FIG. 2 in conjunction with the voltage progressions (or curves) of FIG. 3. Accordingly, the input voltage U consists of the EKG curve (or progression) U1, on which the mains voltage $U_N$ and a pacemaker pulse P are superimposed. As long as no stimulation pulse P yet occurs, the signal processing corresponds to case (b). If a stimulation pulse P occurs, the blanking out proceeds correspondingly to case (c), whereby, however, a peculiar feature is to be observed regarding the behavior of the selective mains frequency filter B1: at the beginning of the blanking out; namely, even in the case of a now-opened switch S1, the selective mains frequency filter is not simply disconnected; on the contrary, the filter B1 continues to oscillate at the previously still present mains frequency. Thus, in this manner, an output voltage U2 is simulated at the output which is equal to the mains frequency according to amplitude and phase. This operation of self-excitation is maintained during the period of blanking out; i.e., as long as the switch S2 is also closed, via the return loop B1, U2, A3, U10, S2, U12, B1. Accordingly, the voltage signal U12 at the input of the selective mains frequency filter B1 thus follows the chronological curve or progression as a function of time as illustrated in FIG. 3F. The phase of the blanking-out of a pacemaker pulse is indicated at PA(t), FIG. 3G. Thus, during the phase of the blanking-out, in the mixing stage A1, the still present mains voltage $U_N$ in the input signal U is compensated by the additionally added simulated signal U2, FIG. 3B. The output voltage U4, FIG. 3D, of the mixing stage A1 thus remains free of mains (or power supply) hum.

Figure 4:
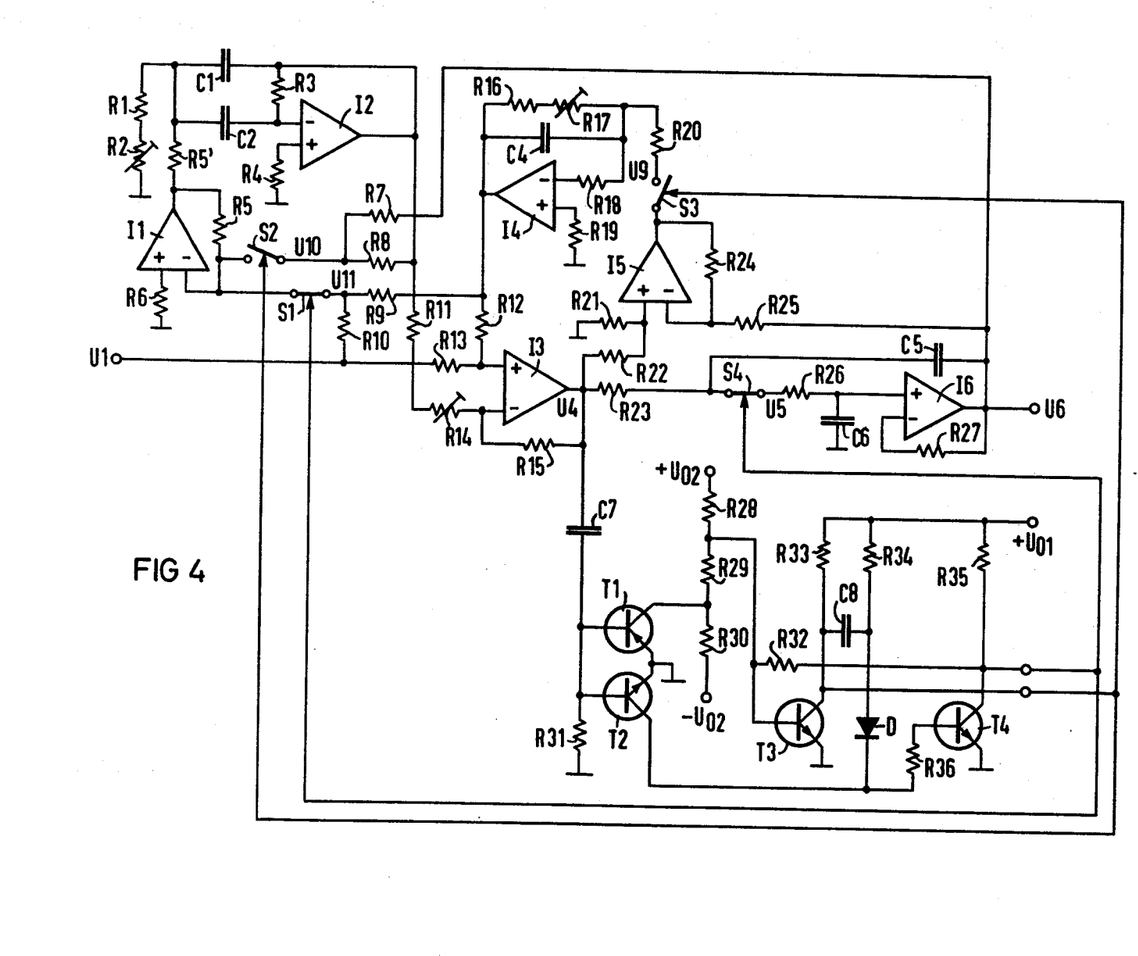
FIG. 4 illustrates a circuit arrangement according to the basic circuit diagram of FIG. 2 in a more detailed representation.

FIG. 4 illustrates a circuit arrangement according to the basic circuit diagram of FIG. 2 in a detailed representation. The following connection exists with the block circuit diagram of FIG. 2:

A1: R11, R12, R13, R14, R15, I3
A2: R9, R10
A3: R7, R8
A4, B4: R21, R22, R24, R25, I5
B1: R1, R2, R3, R4, R5, R6, C1, C2, I1, I2
B2: R28, R29, R30, R31, R32, R33, R34, R35, R36, C7, C8, T1, T2, T3, T4, D1
B3: R23, R26, R27, C5, C6, I6
B5: R16, R17, R18, R19, C4, I4 whereby the components R are ohmic resistances, respectively; the components C, capacitors; the components T, transistors; and the components D, diodes. Components I relate to operational amplifiers and components S relate to analog switches. Specifically, the trimming resistance R2 is the mains frequency filter B1 serves the purpose of adjusting the frequency of the mains frequency filter to 50 Hz. R14 in the mixing stage A1, by contrast, is provided for amplitude adjusting so that, in superposition with the input signal U—likewise comprising interference hum—the interference hum is compensated. With R17 in the time constant member B5, the RC-network C4, R16+R17 is adjusted to the time constant of the overshoot of the heart pacemaker pulse.

As can be further seen from the circuit diagram, the mixing stages A1 through A4 consist of resistance networks which, in cooperation with operational amplifiers, permit a linear voltage superposition. The selective mains frequency filter B1 is an active filter with a series connected inverter I1. The filter is designed in its dimensioning such that, when switch S2 is closed, an active filter results which is operated in proximity to (or near) the transition from the damped to the undamped state. Upon disconnecting the filter from the mains current component $U_N$, the latter filter continues to oscillate at the mains frequency with the previously disconnected amplitude of the mains voltage. The circuit part (or section) for suppression of the heart pacemaker pulse functions according to a procedure similar to that of the circuit arrangement according to the British Pat. No. 1,450,081. The recognition of the pacemaker pulse accordingly proceeds in a known manner corresponding to the slope and amplitude of the input signal. However, as a particular advantage, there is now the additional feature that the recognition of the pacemaker pulse proceeds only subsequent to suppression of the mains frequency, so that large mains frequency amplitudes are not erroneously recognized as a pacemaker pulse. The RC network R34, C8 determines the duration of the phase of a blanking-out of a pacemaker pulse. The duration is dimensioned to approximately t2=9 ms. The capacitor C6 serves the purpose of storing the voltage value preceding the blanking-out.

With the circuit apparatus of FIGS. 2 and 4, the fundamental frequency wave of the mains frequency is preferentially selected and compensated. It is evident that, by means of the parallel-connection of several correspondingly different selective filters, it is also possible to randomly additionally suppress harmonics of the mains frequency. The time constant circuit B5 is specifically designed in the circuit arrangements of FIGS. 2 and 4, for a monomial e-function. It is likewise self-evident that also time constant circuits having a time behavior deviating from an e-function can be utilized, e.g., having such a time function which takes into account the falsification of the e-function of the overshoot of the heart pacemaker pulse specifically by the time constant of an EKG preamplifier during compensation. All these modifications obviously fall within the scope of the invention.

It will be apparent that many further modifications and variations may be effected without departing from the scope of the novel concepts and teachings of the present invention.

I claim as my invention:

1. A method for suppressing noise signals in a useful signal, said method comprising the steps of:
   (a) supplying an input signal comprising a useful signal ($U_1$) which is subject to a noise hum signal ($U_N$) and to noise in the form of narrow noise pulses (P) of high amplitude which may be superimposed on the noise hum signal ($U_N$);
   (b) monitoring said input signal to sense the presence of a narrow noise pulse (P);
   (c) in the absence of the sensing of such a narrow noise pulse (P):
   (c1) supplying the input signal to a noise hum filter (B1) to derive from the input signal a filtered-out interference hum component ($U_2$) corresponding in waveform as a function of time to said noise hum signal ($U_N$); and
   (c2) superimposing on the input signal in opposing relation said filtered-out interference hum component ($U_2$) to tend to suppress the noise hum signal ($U_N$); and
   (d) in the response to the sensing of such a narrow noise pulse (P) pursuant to step (b):
   (d1) suppressing such narrow noise pulse;
   (d2) decoupling the noise hum filter (B1) from the input signal, and switching over said noise hum filter (B1) to self-oscillation operation such that it continues to oscillate with the amplitude and frequency of the previously selected interference hum component without a phase jump to supply an artificially produced oscillation; and
   (d3) superimposing on the input signal said artificially produced oscillation for the purpose of compensation of the interference hum during the period of supression of said narrow noise pulse.

2. A method according to claim 1 with said method further comprising suppressing the narrow noise pulse by blanking out of the input signal during a blanking-out time period, and responding to the sensing of a narrow noise pulse to store a directly preceding value of the useful signal for said blanking-out time period, and supplying the stored value of the useful signal as an initial value of a continuation of the useful signal.

3. A method according to claim 2 further comprising supplying the stored value of the useful signal as a control for the initial value of the self-oscillation operation of the noise hum filter (B1).

4. A method according to claim 2 further comprising delaying the input signal after suppression of the noise hum signal to provide a delayed signal ($U_6$), and obtaining the stored value of the useful signal from the delayed signal.

5. A method according to claim 1 wherein the monitoring of the input signal to sense the presence of a narrow noise pulse takes place after the suppression of the noise hum signal so that a useful signal ($U_4$) purified of the noise hum signal is monitored for the presence of a narrow noise pulse.

6. A method according to claim 1 wherein the suppression of the narrow noise pulse is effected during a blanking-out time period, and during such blanking-out time period generating a voltage waveform ($U_3$) as a function of time corresponding to a waveform of an overshoot response to the narrow noise pulse, and superimposing said voltage waveform ($U_3$) on the input signal to compensate for the overshoot response waveform therein.

7. A method according to claim 6 wherein the voltage waveform ($U_3$) is generated in a time constant circuit (B5) having a time constant according to the time constant of the overshoot response waveform such that the resultant signal after compensation for the overshoot response simulates the input signal as it would have been transmitted in the absence of any noise hum signal and in the absence of the narrow noise pulse.

8. A method according to claim 6 further comprising generating said voltage waveform ($U_3$) in a time constant circuit (B5) during the blanking-out time period such that the voltage value which corresponds to the peak value of the overshoot response waveform is held by the time constant circuit during the blanking-out time period and at the end of the blanking-out time period supplying the voltage waveform with a decaying characteristic corresponding to the decaying characteristic of the overshoot response waveform.

9. A method according to claim 6 further comprising adding the voltage waveform ($U_3$) to the input signal (U) prior to supplying of the input signal to the noise hum filter (B1).

10. Apparatus for suppressing noise signals in a useful signal, said apparatus comprising:
   (a) a measuring signal path having signal input means for supplying to the measuring signal path an input signal comprising a useful signal ($U_1$) which is subject to a noise hum signal ($U_N$) and to noise in the form of narrow noise pulses (P) of high amplitude which may be superimposed on the noise hum signal ($U_N$), and having signal output means;
   (b) monitoring means connected with said signal input means, and comprising an interference pulse peak recognition installation (B2) for monitoring the input signal to sense the presence of a narrow noise pulse (P);
   (c) disconnect switch means (S1) connected with and controlled by said interference pulse peak recognition installation (B2) and maintained in a first condition thereby in the absence of the sensing of such a narrow noise pulse (P), but being shiftable to a second condition,
   (c1) a noise hum filter (B1) operable for filtering out an interference hum component ($U_2$) from the input signal, corresponding in waveform as a function of time to said noise hum signal ($U_N$), having filter input means connected with said signal input means under the control of said disconnect switch means (S1) such that in the absence of sensing of a narrow noise pulse (P) the disconnect switch means (S1) is in said first condition and supplies the input signal to said noise hum filter (B1) so that said noise hum filter (B1) derives from the input signal a filtered-out interference hum component (U2) corresponding in waveform as a function of time to said noise hum signal ($U_N$);

(c2) said noise hum filter (B1) having filter output means connected with said measuring signal path for superimposing on the input signal in opposing relation said filtered-out interference hum component (U2) to tend to suppress the noise hum signal ($U_N$), (d) said interference pulse peak recognition installation (B2) being responsive to sensing of a narrow noise pulse (P) to actuate said disconnect switch means (S1) to said second condition, (d1) said interference pulse peak recognition installation (B2) having output means connected with said measuring signal path for suppressing a narrow noise pulse at said signal output means in response to sensing of such narrow noise pulse by said interference pulse peak recognition installation (B2) pursuant to the monitoring of said input signal, (d2) said disconnect switch means (S1) in said second condition decoupling the noise hum filter (B1) from said signal input means, and said noise hum filter (B1) having switchover means connected with and controlled by said interference pulse peak recognition installation (B2) and responsive to the sensing of a narrow noise pulse thereby to switch over said noise hum filter (B1) to self-oscillation operation such that it continues to oscillate with the amplitude and frequency of the previously selected interference hum component (U2) without a phase jump to supply an artificially produced oscillation; and (d3) said filter output means of said noise hum filter (B1) during the suppression of a narrow noise pulse superimposing on the input signal said artificially produced oscillation for the purpose of compensation of the interference hum during the period of suppression of said narrow noise pulse.

11. Apparatus according to claim 10 with said noise hum filter (B1) being an active filter which is operated close to the transition from the damped to the undamped state, said switchover means comprising a feedback switch (S2) which is closed to operate said active filter in a self-excitation mode.

12. Apparatus according to claim 10, further comprising mixing means (A2) having a first input connected with said signal input means for receiving the useful signal (U1) which is subject to a noise hum signal ($U_N$), and having a second input and an output; and a time constant circuit (B5) connected with the second input of the mixing means (A2) for supplying thereto a compensation signal for compensating for the overshoot of a narrow noise pulse;

the output of said mixing means (A2) being connected via the disconnect switch means (S1) with the filter input means of the noise hum filter (B1).

13. Apparatus according to claim 10, with said measuring signal path including mixing means (A1) having a first input connected with said signal input means for receiving a useful signal (U1) which is subject to a noise hum signal ($U_N$) and to noise in the form of narrow noise pulses (P), having a second input connected with said filter output means for receiving the filtered-out interference hum component, having a third input, and an output;

time constant circuit means (B5, S3, B4, A4) connected with said signal output means (U6) and with the output of said mixing means (A1) and operable for generating a compensation signal (U3) for compensating for an overshoot waveform portion of a narrow noise pulse, and connected with the third input of said mixing means (A1) for supplying the compensation signal (U3) thereto;

said interference pulse peak recognition installation (B2) being connected with the output of said mixing means (A1).

14. Apparatus according to claim 10, with said disconnect switch means (S1) being interposed between the signal input means and the filter input means;

said switchover means comprising a feedback switch (S2);

said noise hum filter (B1) having a feedback circuit extending between said filter output means and said filter input means, said feedback circuit including said feedback switch (S2) and mixing means (A3) having a first input connected with the filter output means and having a second input; and said measuring signal path including signal storage means (S4, B3) responsive to sensing of a narrow noise pulse (P) by said interference pulse peak installation (B2) to store a voltage value (U6) of the useful signal, said signal storage means (S4, B3) having an output connected with the second input of said mixing means (A3) and with said signal output means.

15. Apparatus according to claim 10 with time constant circuit means for forming a control path, and comprising an overshoot control switch (S3) connected with and controlled by said interference pulse peak recognition installation (B2) for assuming a closed condition when a narrow noise pulse (P) is sensed thereby, a time constant circuit (B5) having an input connected with said overshoot control switch (S3) and having an output connected with the filter input means under the control of said disconnect switch means (S1), and a comparator (B4) having input means (A4) connected with said signal output means (U6) and operable for sensing a peak value of an overshoot waveform portion of a narrow noise pulse, and having an output connected with the input of said time constant circuit (B5) under the control of said overshoot control switch (S3), said time constant circuit (B5) being responsive to closed condition of said overshoot control switch (S3) to rapidly charge to the peak value of the overshoot waveform portion.

16. Apparatus according to claim 15, with the measuring signal path including first mixing means (A1) having a first input connected with said signal input means, having a second input connected with the filter output means, having a third input connected with the output of said time constant circuit (B5), and having an output, said input means of said comparator (B4) comprising further mixing means (A4) having a first input connected with the output of said first mixing means (A1), having a second input connected with the signal output means (U6), and having an output connected with said comparator (B4) so that the comparator (B4) is connected with the signal output means (U6) via the further mixing means (A4); and said time constant circuit means being operable for supplying to the measuring signal path via said first mixing means (A1) a compensation signal (U3) for compensating for an overshoot waveform portion of the input signal following a narrow noise pulse, said further mixing means (A4), said comparator (B4) and said time constant circuit (B5) forming a closed control loop with the overshoot control switch (S3) in the closed condition for generating said compensation signal.

17. Apparatus according to claim 16 with said measuring signal path including signal storage means (S4, B3) connected with the output of the first mixing means (A1) for receiving and storing a signal (U4) purified of the noise hum signal ($U_N$), and having an output connected with the second input of said further mixing means (A4) supplying a stored signal thereto.

* * * * *